(12) United States Patent
Lukay

(10) Patent No.: US 6,776,028 B1
(45) Date of Patent: Aug. 17, 2004

(54) INDUCTION SENSOR VISCOMETER

(75) Inventor: Richard F. Lukay, Houston, TX (US)

(73) Assignee: OFI Testing Equipment, Inc., Houston, TX (US)

( * ) Notice: Subject to any disclaimer, the term of this patent is extended or adjusted under 35 U.S.C. 154(b) by 0 days.

(21) Appl. No.: 10/425,228

(22) Filed: Apr. 29, 2003

(51) Int. Cl.[7] .............................................. G01N 11/14
(52) U.S. Cl. ..................... 73/54.28; 73/54.33; 73/54.35; 73/54.38
(58) Field of Search ............................. 73/54.23, 54.28, 73/54.31, 54.32, 54.33, 54.34, 54.35, 54.36, 54.38

(56) References Cited

U.S. PATENT DOCUMENTS

| | | | |
|---|---|---|---|
| 3,751,975 A | | 8/1973 | Katsura ..................... 73/54.38 |
| 4,043,183 A | | 8/1977 | Higgs et al. |
| 4,175,425 A | | 11/1979 | Brookfield |
| 4,448,061 A | | 5/1984 | Brookfield ................. 73/54.33 |
| 4,472,963 A | * | 9/1984 | Gyer et al. ................. 73/54.34 |
| 4,484,468 A | | 11/1984 | Gau et al. ................... 73/54.35 |
| 4,557,142 A | * | 12/1985 | Hensley et al. .......... 73/152.19 |
| 6,167,752 B1 | * | 1/2001 | Raffer ....................... 73/54.28 |
| 6,484,567 B1 | * | 11/2002 | Hajduk et al. ............. 73/54.37 |
| 6,492,911 B1 | * | 12/2002 | Netzer ................... 340/870.37 |

* cited by examiner

*Primary Examiner*—Daniel S. Larkin
(74) *Attorney, Agent, or Firm*—Keeling Hudson LLC

(57) ABSTRACT

A rotational viscometer includes a cylindrical bob attached to a bob axle, a concentric sleeve exterior of the bob, a motor for inducing rotation in the sleeve, a biasing spring attached to the bob axle for resisting axle rotation, and a measurement system comprising an electric field transmitter, an electric field receiver and a rotor extending intermediate the transmitter and receiver. The rotor is attached to the bob axle so that rotation of the bob axle and the rotor presents a measurable deviation of the electrical field received by the electrical field receiver. A processor calculates the angle of displacement of the bob from that sine and cosine of the received electrical field and transmits readable output in the form of a sample viscosity value to a display.

27 Claims, 3 Drawing Sheets

INDUCTION SENSOR VISCOMETER

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

Field of the Invention

The invention is generally related to viscometers and more specifically to viscometers employing an inductive displacement sensor to detect the angle of displacement of a bob used to measure viscosity of a tested fluid.

Description of the Related Art

Viscometers are known to use a variety of configurations to measure rheological properties of a fluid. One frequently employed configuration is a rotational Couette geometry viscometer comprised of a cylindrical bob positioned on a bob axle and a concentric sleeve exterior of the bob suspended from a viscometer housing into a container holding a sample of the fluid to be tested. As the concentric sleeve is rotated at a determined speed, a specified shear rate is exerted on the fluid near the face of the rotor and rotation of the bob is induced. A biasing spring resists rotation of the bob and axle. The resulting deflection of the bob in response to the rotation of the sleeve is an indicator of the viscosity of the fluid intermediate the bob and sleeve.

Prior art viscometers include:

U.S. Pat. No. 3,751,975 issued to Katsura on Aug. 14, 1973, discloses a pair of magnetic electrical signal generators mounted on opposite ends of the torsion area of a torsion bar. When the torsion bar is rotated with one end submerged in a sample fluid, comparison of the difference between the generated signals provides a direct relationship to the viscosity of the sample fluid.

U.S. Pat. No. 4,043,183 issued to Higgs et al. on Aug. 23, 1977, discloses a consistometer for continuously measuring the viscosity of the liquid in a stream. When a reference sensor outside the stream and a detector sensor within the stream are simultaneously spun in relationship to respective stationary sensors, comparison of the difference between the reference signal and the detected signal provides a direct relationship to the viscosity of the liquid in the stream.

U.S. Pat. No. 4,175,425 issued to Brookfield on Nov. 27, 1979, discloses a viscometer having a drive cylinder and a driven cylinder attached to a resistance unit, which is linked to a magnetic transducer readout device. The patent states that the inventive structure works with other types of readout devices.

U.S. Pat. No. 4,448,061 issued to Brookfield on May 15, 1984, and reexamined on Oct. 9, 1990 and Nov. 21, 1995, discloses a rotational viscometer, which uses a rotor-stator configuration to produce continuous out-feed of electric signals of strengths varying with the viscosity of the liquid being monitored.

U.S. Pat. No. 4,484,468 issued to Gau et al. on Nov. 27, 1984, discloses an automatic rotational viscometer comprised of a rotated or torqued sleeve. The sleeve applies rotation to a bob, monitored by an optical encoder, which measures the angular displacement of the bob from the zero azimuth position and continues to be sensed until the angle is stabilized.

It would be an improvement to the field to adapt a viscometer with a linear inductive angular displacement sensor to more precisely quantify the amount of force imparted to the bob by the fluid in relationship to the rotation of the bob axle.

BRIEF SUMMARY OF THE INVENTION

Accordingly, the objects of my invention are to provide, among other things, a rotational viscometer that:

provides a high degree of accuracy over the operational range;

comprises mechanically and electrically simple configuration;

is tolerant of variations in environmental conditions; and provides reduced friction forces to the bob and axle.

Other objects of my invention will become evident throughout the reading of this application.

My invention is a rotational viscometer, which employs an electrical field sensor to measure the induced angle of rotation of a bob by a sample substance. The viscometer includes a generally circular bob attached to a bob axle, a concentric sleeve exterior of the bob, a motor for inducing rotation in the sleeve, a biasing spring attached to the bob axle for resisting axle rotation, and a measurement system comprising an electric field transmitter, an electric field receiver and a rotor extending intermediate the transmitter and receiver. The rotor is attached to the bob axle so that rotation of the bob axle and the rotor results in a measurable deviation of the received electrical field. The processor calculates the angle of displacement of the bob and transmits readable output of a sample characteristic in accordance with determined calculations based on, among other things, the sleeve rotation velocity and the bob displacement.

DESCRIPTION OF THE INVENTION

Figure 1:
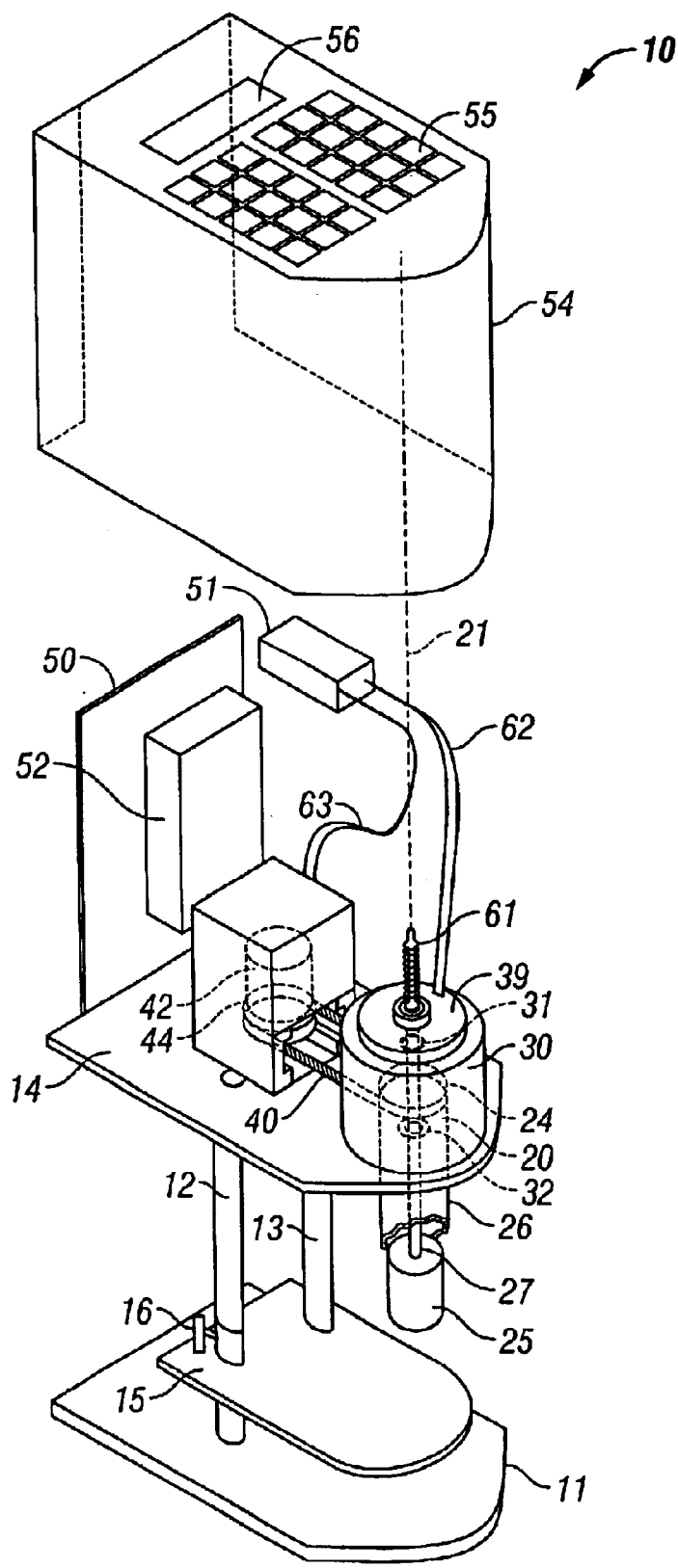
FIG. 1 is a perspective view of the viscometer of the present invention.
Figure 2:
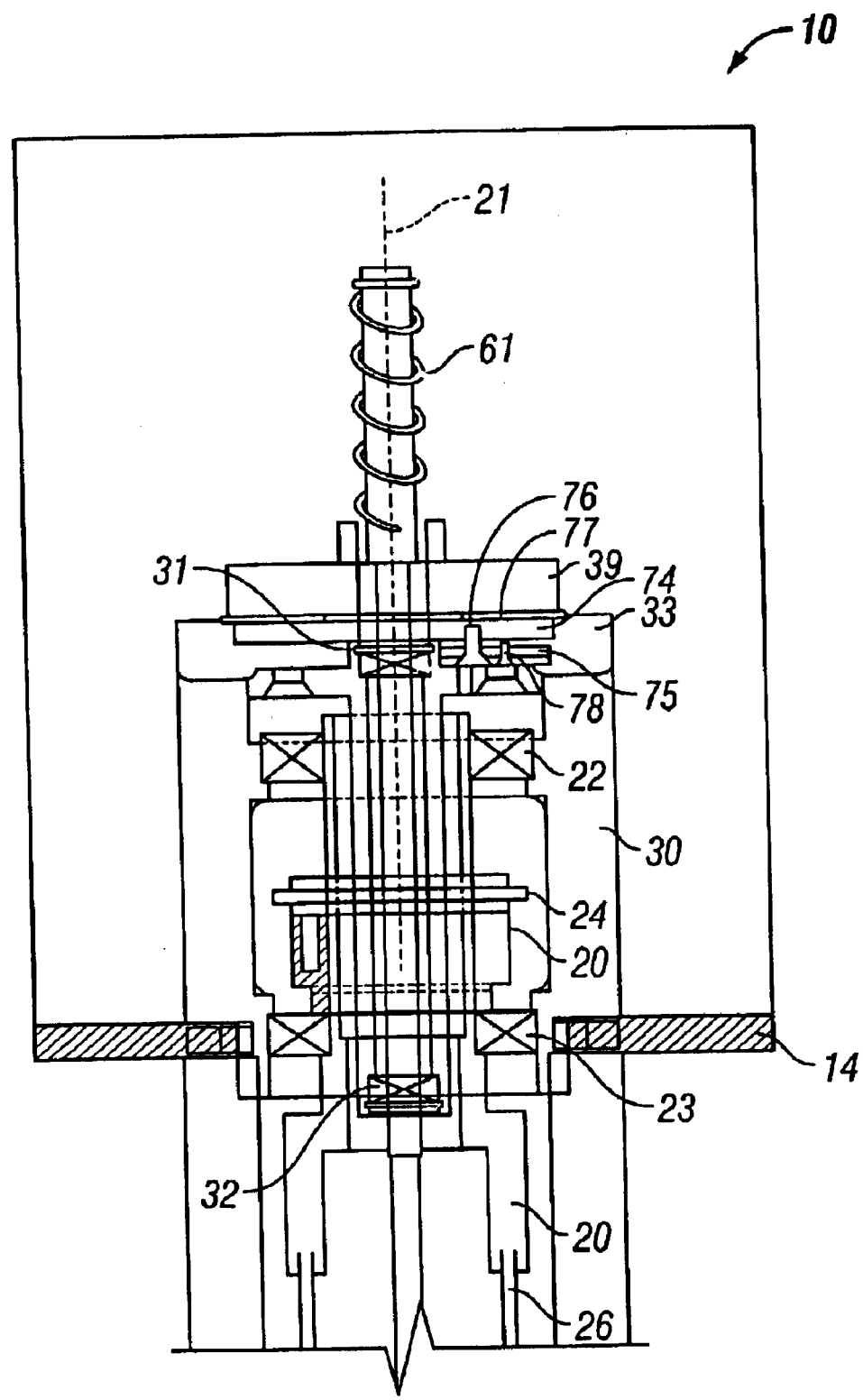
FIG. 2 is a detailed partial cross-sectional view of the viscometer.

Referring to FIG. 1 and FIG. 2, the viscometer 10 of the present invention is depicted. The viscometer 10 includes a base 11, upstanding legs 12 and 13, each supported by base 11, an upper structure 50 and a moveable stage 15 intermediate base 11 and upper structure 50. Legs 12 and 13 extend upright to a platform 14 of upper structure 50. Platform 14 is parallel to the base 11. Stage 15 is supported on legs 12 and 13 and vertically moveable on legs 12 and 13. Stage 15 may be fixed at a position on legs 12 and 13 by a locking nut 16.

Upper structure 50 includes a support structure 30 attached to platform 14. Support structure 30 supports vertical upper sleeve 20 and vertical bob axle 27 in a vertical orientation and normal to stage 15. Support structure 30 further supports encoder 39 in a fixed position in relation to bob axle 27.

A cylindrical bob 25 is fixedly supported on bob axle 27. Bob 25 and bob axle 27 are concentrically oriented about a common bob axis 21. Axle 27 is supported in vertical orientation by upper axle bearings 31 and lower axle bearings 32. Each of upper axle bearings 31 and lower axle bearings 32 are supported by support structure 30.

Upper sleeve 20 is a hollow, generally cylindrical structure coaxially oriented with bob axle 27. Upper sleeve 20 is rotatable around axis 21, and may be described as coaxially concentric to bob axle 27 and bob 25. Upper sleeve 20 is retained in stable vertical position by upper sleeve bearings 22 and lower sleeve bearings 23.

Upper sleeve 20 extends below platform 14. A lower sleeve 26 is removably connected to upper sleeve 20. Connection may be by threading or other suitable means. Lower sleeve 26 is also coaxially concentric with bob axis 21.

A motor 42 and drive belt 40 are provided for rotation of upper sleeve 20 and lower sleeve 26. In an exemplary embodiment, drive belt 40 contains links 44 that engage splines (not shown) of a motor gear (not shown) and sleeve gear 24. In the exemplary embodiment, sleeve gear 24 is cylindrical and is fitted around upper sleeve 20 coaxially concentric with axis 21. The motor 42 is operable at various speeds suitable to impart a desired rotation frequency of upper sleeve 20 and lower sleeve 26. In the exemplary embodiment, a power converter 52 is provided to convert alternating current power to direct current for supplying power to motor 42.

Figure 3:
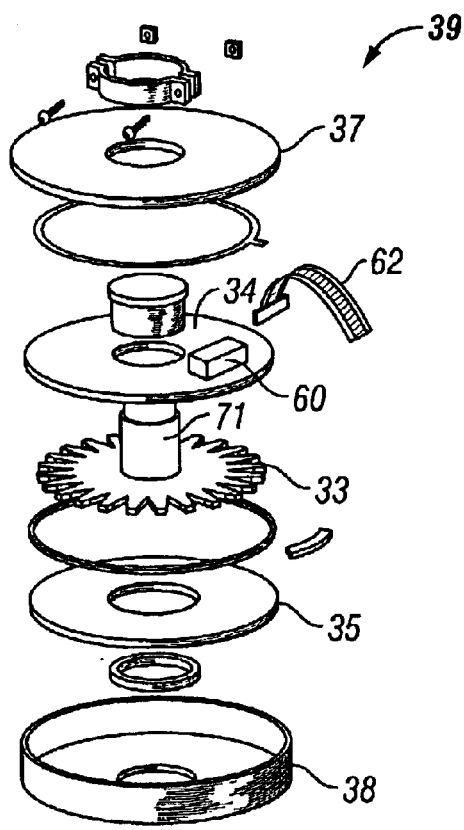
FIG. 3 is an exploded view of a rotary electrical encoder.
Figure 4:
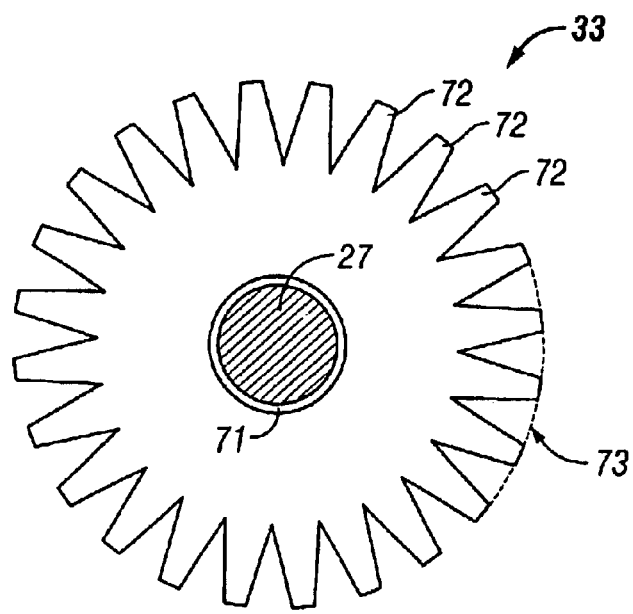
FIG. 4 is a detailed view of a rotary electrical encoder rotor.

Referring to FIGS. 1 through 3, electrical assembly 39 is supported by support structure 30 and by encoder cradle 74. Electrical assembly 39 includes an upper housing 37, a lower housing 38, an electrical field transmitter 35, an electrical field receiver 34 and a rotor 33. Upper housing 37, lower housing 38, electrical field transmitter 35 and electrical field receiver 34 are each positioned in a fixed position in relation to support structure 30 and axle 27. Rotor 33 is positioned intermediate electrical field transmitter 35 and electrical field receiver 34. Rotor 33 is attached to axle 27 and revolves with axle 27. Rotor 33 does not contact either of electrical field transmitter 35 or electrical field receiver 34. Referring to FIG. 4, rotor 33 includes a rotor hub 71 attached to axle 27, a rotor outer rim 73 and rotor spokes 72 extending intermediate rotor hub 71 and rotor rim 73. A suitably structured electrical field receiver 34 is sold by Netzer Precision Motion Sensors Ltd. and is identified as a rotary electric encoder.

An electrical connector 60 and connector wiring 62 communicate data received at electrical field receiver 34 to processor 51. Control wiring 63 connecting processor 51 and motor 42 allow for control of motor 42. Processor 51 is operationally attached to input interface 55 and to output interface 56. Such attachment may be by circuit boards and wiring (not shown) known in the art. In an exemplary embodiment, processor 51 includes read only memory and random access memory, allowing processor 51 to control multiple predetermined functions and to control functions determined by operator input.

A torsion spring 61 is positioned intermediate electrical assembly 39 and viscometer housing 54. Spring 61 biases the axle 27 in a determined position and resists rotational movement of axle 27. Other torsioning devices known in the field may be used, for example axially torsioned wire, metal strips or plastic strips.

Referring to FIG. 2 and FIG. 3, extension arm 75 is attached to axle 27 intermediate a lower surface 77 of cradle 74 and an upper surface 78 of support structure 30. Arm 75 is normal to axis 21 and correspondingly parallel to stage 15 and base 11. A removable stop 76 extends upwardly from cradle 74 such that arm 75 will engage stop 76 upon rotation of axle 27. Stop 76 may therefore act as a bar to limit rotation of axle 27 if desired. Upon removal of stop 76 from cradle 74, rotation of axle 27 will not be limited by stop 76. An exemplary form of stop 76 comprises a screw insertable in a threaded opening in cradle 74.

In operation, a cup (not shown) containing a sample of fluid to be tested (not shown) is placed on stage 15 and stage 15 is raised to a position where the bob 25 and the lower sleeve 26 are immersed in the sample. Sufficient distance is provided between base 11 and platform 14 to allow a sample container (not shown) to be placed on stage 15 and raised with stage 15 to a proper position in relation to bob 25 and lower sleeve 26. The specific configuration of bob 25, lower sleeve 26 and the extent of immersion may be dictated by industry practice or accepted conventions for the types of fluid to be tested.

The motor 42 is operable at various speeds in order to induce a specified speed of rotation in upper sleeve 20 and lower sleeve 26. Such speed is controlled by a motor controller (not shown) known in the art.

Rotation of the lower sleeve 26 induces a rotational force in the sample, which rotational force is transmitted to the bob 25 and the spring 61 biasing axle 27. The extent of rotation of bob 25 in response to rotational force of the sample is a function of, among other things, the viscosity of the sample and the resistance force of the spring 61. As the spring 61 resistance may be determined within the range of forces applied, the bob 25 angular rotation may comprise an accurate indication of sample viscosity.

Rotation of bob 25 results in corresponding rotation of rotor 33. Rotation of rotor 33 results in measurable distortion of a patterned electrical field generated by electrical field transmitter 35 and received by electrical field receiver 34. In the exemplary embodiment, such distortion is output to processor 51 as continuously varying voltages proportional to the sine and cosine of the measured angle of angular displacement of axle 27. In the exemplary embodiment, processor 51 converts such voltages to digital values at a determined integration and conversion rate.

As the patterned electrical field is generated over a suitably large area and the rotation of each of the plurality of rotor spokes 72 each generates a distortion in the electrical field, the precision of the resulting measurement is enhanced. Additionally, the lack of contact between the measuring indicator, the rotor 33 and the electrical field transmitter 35 and electrical field receiver 34 reduces error in the resulting measurement and eliminates mechanical variations of heat, environmental moisture and torque on measurement mechanical components.

An input interface 55 communicating with processor 51 is provided for entry of instructions to processor 51. An output display 56 communicating with processor 51 is also provided. The cover 54 is placed on the platform 14 to enclose the apparatus. In the exemplary embodiment, input interface 55 comprises a keyboard, said keyboard including a plurality of keys that define numerical values and a plurality of keys that identify determined functions to be performed through processor 51. In an exemplary embodiment, processor 51 is operably connected to motor controller (not shown) to operate motor 42 at predetermined speeds. In an exemplary embodiment, processor 51 includes read only memory and random access memory to allow processor to receive operator input, control motor speed, receive input from electrical field receiver 34, calculate sample properties and transmit to output display 56 sample properties. Processor 51 may further display operational information, such as sleeve rotation speed and angular deflection of the bob. Predetermined function calculations include a calibrate function, a set up function, a sample viscosity, and a sample gel strength. Various functions may be provided for differing types of material, such as drilling mud or cement.

In an alternate embodiment, an external processor (not shown), such as a computer, interfaces with processor 51. In this embodiment, the external processor can communicate entry of-instructions to processor 51. Additionally, processor 51 can transmit output of sample properties to the external processor. The external processor may directly interface with processor 51 or processor 51 may interface with a network (not shown), such as the Internet, in which the external processor is also interfaced, thereby allowing instructions to and output from processor 51 to be entered and monitored from a location remote of the viscometer 10 through the network. The foregoing disclosure and description of the invention is illustrative and explanatory thereof Various changes in the details of the illustrated construction may be made within the scope of the appended claims without departing from the spirit of the invention. The present invention should only be limited by the following claims and their legal equivalents.

What is claimed is:

1. A rotational viscometer, comprising:
   a cylindrical bob attached to a bob axle;
   said bob having a bob axis;
   a rotatable sleeve concentric with said bob axis;
   a motor operably connected to said sleeve for rotating said sleeve;
   a motor controller operably connected to said motor for rotating said sleeve at a determined speed;
   a torsion element for resisting rotation of said bob;
   a rotational electrical field encoder for measuring electrical field variance resulting from rotation of said bob;
   an input interface;
   an output interface;
   a processor operably communicating with said input interface, said encoder, and said output interface;
   an arm extending outwardly from said bob axle;
   a removeable stop capable of engaging said arm; and
   said stop preventing further rotation of said bob axle upon engagement of said arm with said stop.

2. The apparatus of claim 1, further comprising:
   said input interface comprising an external processor;
   said external processor operable to input instructions to said processor; and
   said output interface comprising said external processor.

3. The apparatus of claim 2, wherein said external processor is locate remote from said processor.

4. An apparatus according to claim 1, further comprising:
   said processor operably communicating with said motor controller.

5. An apparatus according to claim 1, further comprising:
   said encoder comprising an electrical field transmitter, an electrical field receiver, and a rotor;
   said rotor intermediate said transmitter and said receiver; and
   said rotor attached to said bob axle whereby said rotor is rotated in relation to said electrical field transmitter and said receiver upon rotation of said bob axle.

6. An apparatus according to claim 5, further comprising:
   said electrical held receiver producing an output voltage signal proportional to a sine and cosine of a measured angle of rotation of said bob; and
   said processor converting said output voltage signal to a displacement angle of said bob.

7. An apparatus according to claim 5, further comprising:
   said receiver and said transmitter fixedly supported on a support structure;
   said rotor fixedly supported on said bob axle; and
   said rotor comprising a plurality of rotor spokes whereby rotation of said bob axle causes said plurality of rotor spokes to rotate intermediate said transmitter and said receiver.

8. An apparatus according to claim 7, further comprising:
   said electrical field receiver producing an output voltage signal proportional to a sine and cosine of a measured angle of rotation of said bob;
   said input interface responsive to externally generated commands;
   said processor operable to control said motor controller;
   said processor operable to receive said output voltage signal from said electrical receiver;
   said processor operable to convert said output voltage signal to digital values;
   said processor operable to calculate an angle of displacement of said bob;
   said processor operable to calculate a sample value as a function of said calculated angle of displacement; and
   said processor operable to transit said calculated sample value to said output interface.

9. The apparatus of claim 8, further comprising;
   said input interface comprising an external processor;
   said external processor operable to input instructions to said processor; and
   said output interface comprising said external processor.

10. The apparatus of claim 9, wherein said external processor is located remote from said processor.

11. An apparatus according to claim 7, further comprising:
    said processor programmable to include instructions for operating said motor controller, calculating at least one sample value and transmitting said at least one sample value to said output interface.

12. A device for measuring bob rotation of a rotational viscometer of the type having a cylindrical bob attached to a bob axle, said bob having a bob axis, a rotatable sleeve concentric with said bob axis, a motor operably connected to said sleeve for rotating said sleeve, a motor controller operably connected to said motor for rotating said sleeve at a determined speed, a torsion clement for resisting rotation of said bob, said device comprising:
    a rotational electrical field encoder for measuring electrical field variance resulting from rotation of said bob;
    an input interface;
    an output interface;
    a processor operable communicating with said input interface, said encoder, and said output interface;
    said encoder comprising an electrical field transmitter, an electrical field receiver, and a rotor;
    said rotor intermediate said transmitter and said receiver;
    said rotor attached to said bob axle whereby said rotor is rotated in relation to said electrical field transmitter and said receiver upon rotation of said bob axle;
    said receiver and said transmitter fixedly supported on support structure; and
    said rotor fixedly supported on said bob axle.

13. The device according to claim 12, wherein:
said input interface comprising a key pad;
said keypad operable to input instruction to said processor; and
said output interface comprising a visual display of designated symbols.

14. The device according to claim 12, further comprising:
said input interface comprising an external processor;
said external processor operable to input instructions to said processor; and
said output interface comprising said external processor.

15. The device according to claim 14, wherein said external processor is located remote from said processor.

16. The device according to claim 12, further comprising:
said electrical field receiver producing an output voltage signal proportional to a sine and cosine of a measured angle of rotation of said bob; and
said processor converting said output voltage signal to a displacement angle of said bob.

17. The device according to claim 12, further comprising:
said rotor comprising a plurality of rotor spokes whereby rotation of said bob axle causes said plurality of rotor spokes to rotate intermediate said transmitter and said receiver.

18. The device according to claim 17, further comprising:
said electrical field receiver producing an output voltage signal proportional to a sine and cosine of a measured angle of rotation of said bob;
said input inter responsive to externally generated commands;
said processor operable to control said motor controller;
said processor operable to receive said output voltage signal from said electrical receiver;
said processor operable to convert said output voltage signal to digital values;
said processor operable to calculate an angle of displacement of said bob;
said processor operable to calculate a sample value as a function of said calculated angle of displacement; and
said processor operable to transmit said calculated sample value to said output interface.

19. The device according to claim 17, further comprising:
said processor programmable to include instructions for operating said motor controller, calculating at least one sample value and transmitting said at least one sample value to said output interface.

20. The device according to claim 17, further comprising:
said input interface comprising a key pad;
said key pad operable to input instructions to said processor; and
said output interface comprising a visual display of designated symbols.

21. The device according to claim 17, further comprising:
said input interface comprising an external processor;
said external processor operable to input instructions to said processor; and
said output interface comprising said external processor.

22. A rotational viscometer, comprising:
a cylindrical bob attached to a bob axle;
said bob having a bob axis;
a rotatable sleeve concentric with said bob axis;
a motor operably connected to said sleeve for rotating said sleeve;
a motor controller operably connected to said motor for rotating said sleeve at a determined speed;
a torsion element for resisting rotation of said bob;
a rotational electrical field c for measuring electrical field variance resulting from rotation of said bob;
an input interface;
an output interface;
a processor operably communicating with said input interface, said encoder, and said output interface;
said encoder comprising an electrical field transmitter, an electrical field receiver, and a rotor;
said rotor intermediate said transmitter and said receiver;
said rotor attached to said bob axle whereby said rotor is rotated in relation to said electrical field transmitter and said receiver upon rotation of said bob axle;
said receiver and said transmitter fixedly supported on a support structure;
said rotor fixedly supported on said bob axle.

23. An apparatus according to claim 22, further comprising:
said rotor comprising a plurality of rotor spokes whereby rotation of said bob axle causes said plurality of rotor spokes to rotate intermediate said transmitter and said receiver.

24. An apparatus according to claim 23, further comprising:
said electrical field receiver producing an output voltage signal proportional to a sine and cosine of a measured angle of rotation of said bob;
said input interface responsive to externally generated commands;
said processor operable to control said motor controller;
said processor operable to receive said output voltage signal from said electrical receiver;
said processor operable to convert said output voltage signal to digital values;
said processor operable to calculate an angle of displacement of said bob;
said processor operable to calculate a sample value as a function of said calculated angle of displacement; and
said processor operable to transmit said calculated sample value to said output interface.

25. The apparatus of claim 24, further comprising:
said input interface comprising an external processor;
said external processor operable to input instructions to said processor; and
said output interface comprising said external processor.

26. The apparatus of claim 25, wherein said external processor is located remote from said processor.

27. An apparatus according to claim 23, further comprising:
said processor programmable to include instructions for operating said motor controller, calculating at least one sample value and transmitting said at least one sample value to said output interface.

* * * * *

UNITED STATES PATENT AND TRADEMARK OFFICE
CERTIFICATE OF CORRECTION

PATENT NO.        : 6,776,028 B1                                        Page 1 of 1
APPLICATION NO.   : 10/425228
DATED             : August 17, 2004
INVENTOR(S)       : Richard F. Lukay It is certified that error appears in the above-identified patent and that said Letters Patent is hereby corrected as shown below:

In column 8, line 7, claim 22: please correct "c" to read --encoder--.

Signed and Sealed this

Twentieth Day of April, 2010

David J. Kappos
*Director of the United States Patent and Trademark Office*